(12) United States Patent
Linder et al.

(10) Patent No.: US 9,103,802 B2
(45) Date of Patent: Aug. 11, 2015

(54) METHOD AND ARRANGEMENT FOR CRACK DETECTION IN A METALLIC MATERIAL

(71) Applicants: Sten Linder, Trosa (SE); Lennart Thegel, Vasteras (SE)

(72) Inventors: Sten Linder, Trosa (SE); Lennart Thegel, Vasteras (SE)

(73) Assignee: ABB TECHNOLOGY AG (CH)

( * ) Notice: Subject to any disclaimer, the term of this patent is extended or adjusted under 35 U.S.C. 154(b) by 484 days.

(21) Appl. No.: 13/632,779

(22) Filed: Oct. 1, 2012

(65) Prior Publication Data

US 2013/0085685 A1   Apr. 4, 2013

(30) Foreign Application Priority Data

Sep. 29, 2011 (EP) .................................. 11183351

(51) Int. Cl.
*G06F 19/00* (2011.01)
*G01N 27/90* (2006.01)

(52) U.S. Cl.
CPC ................................. *G01N 27/9046* (2013.01)

(58) Field of Classification Search
CPC ..... B60R 21/0136; G01N 27/902; G01B 7/24
USPC .................... 702/38, 150–155, 160, 182–185
See application file for complete search history.

(56) References Cited

U.S. PATENT DOCUMENTS

| | | | |
|---|---|---|---|
| 4,475,083 A | 10/1984 | Linder | |
| 5,391,988 A | 2/1995 | Kitagawa | |
| 6,291,992 B1 | 9/2001 | van Andel et al. | |
| 6,661,224 B1 | 12/2003 | Linder | |
| 7,495,433 B2 | 2/2009 | Daalmans et al. | |
| 8,109,150 B2 * | 2/2012 | Sato et al. | 73/799 |
| 2003/0062892 A1 | 4/2003 | Kachelries et al. | |

FOREIGN PATENT DOCUMENTS

| | | |
|---|---|---|
| CN | 1239023 A | 12/1999 |
| DE | 3217519 A1 | 11/1983 |
| EP | 0152904 A2 | 8/1985 |
| FR | 2714470 A1 | 6/1995 |
| JP | 1316655 A | 12/1989 |
| JP | 3267754 A | 11/1991 |
| JP | 4070561 B | 11/1992 |
| JP | 7078489 B | 8/1995 |

(Continued)

OTHER PUBLICATIONS

European Search Report; Application No. EP 11 18 3351; Completed: Dec. 21, 2011; 4 pages.

*Primary Examiner* — Edward Raymond

(74) *Attorney, Agent, or Firm* — Whitmyer IP Group LLC

(57) ABSTRACT

A method of determining a crack depth of a crack in a metallic material including the steps: feeding a current with a first magnitude to a transmitter coil for generating a magnetic field in the metallic material; controlling the current such that it obtains a second magnitude when the magnetic field is estimated to have penetrated deeper than a deepest crack depth desired to be measured in the metallic material; detecting the magnetic field by means of a receiver coil; determining a first characteristic value of the signal in a first time range; determining a second characteristic value of the signal in a second time range after the first time range; and determining a possible presence of a crack and its crack depth based on the first characteristic value and the second characteristic value.

12 Claims, 3 Drawing Sheets

(56) References Cited

FOREIGN PATENT DOCUMENTS

| | | | |
|---|---|---|---|
| JP | 9281082 | A | 10/1997 |
| JP | 10160710 | A | 6/1998 |
| JP | 11326284 | A | 11/1999 |
| JP | 2000514559 | A | 10/2000 |
| JP | 2001033429 | A | 2/2001 |
| JP | 2003503683 | A | 1/2003 |
| JP | 2006200954 | A | 8/2006 |
| JP | 2007033420 | A | 2/2007 |
| JP | 2009079984 | A | 4/2009 |
| JP | 2010085298 | A | 4/2010 |
| WO | 8802842 | A1 | 4/1988 |

* cited by examiner

METHOD AND ARRANGEMENT FOR CRACK DETECTION IN A METALLIC MATERIAL

FIELD OF THE INVENTION

The present disclosure generally relates to quality inspection of a metallic material, and in particular to crack detection in the surface of a metallic material utilising electromagnetic induction.

BACKGROUND OF THE INVENTION

A known method of contactless crack measurements of a metallic material is to utilise optical means. The metallic material may be irradiated by light wherein a crack may be detected by means of an optical sensor such as a camera. Drawbacks with optical methods are that it is not possible to detect cracks which are not visible on the surface of the metallic material, and that colour variations in the metallic material may be interpreted as cracks by the optical sensor. Optical methods have been proved to be difficult to use in other applications than for inspection of completely clean and smooth metal surfaces.

Inspection of metallic materials in for instance steel production has been made utilising inductive techniques. When using an inductive technique a current is induced in the metallic material, e.g. a slab or a metal sheet, by means of a time-varying magnetic field generated by a transmitter coil fed with a likewise time-varying current. When the induced current encounters a crack in the metallic material, the crack constitutes an obstacle to the induced current. As a result, the crack alters the induced current at the crack as compared to a metallic material without a crack. The altered current provides a change in the magnetic field around the current. The change in the magnetic field is measured by a receiver coil, whereby it can be determined that a crack is present in the inspected surface portion of the metallic material.

There are several drawbacks with the induction techniques used today for crack detection in metallic materials. Several parameters other than a crack depth may for example influence changes in the magnetic field. Examples of such parameters are the distance between the coils and the object to be measured, magnetic oxide on the surface of the object, changes in the physical characteristics in the material of which the object is made, the position of the crack in relation to the coils, and the length of the crack. To this end, when a change is measured by a receiver coil, it may be difficult to determine whether this change is due to the crack depth or another parameter which may vary. Due to the fact that it is difficult to keep influencing parameters constant, it has been difficult to use inductive techniques for crack inspection of irregular surfaces such as casted metallic surfaces.

SUMMARY OF THE INVENTION

In view of the above, a general object of the present disclosure is to provide an inductive method for determining a crack depth in a metallic material.

Another object of the present disclosure is to provide an inductive method for determining a crack length in a metallic material.

Yet another object is to provide inductive crack depth measurements of a metallic material where other process parameters than the actual crack depth has minimal influence on the measurements.

Thus, according to a first aspect of the present disclosure there is provided a method of determining a crack depth of a crack in a metallic material, the method comprising:
  feeding a current with a first magnitude to a transmitter coil for generating a magnetic field in the metallic material,
  controlling the current such that it obtains a second magnitude when the magnetic field is estimated to have penetrated deeper than a deepest crack depth desired to be measured in the metallic material,
  detecting the magnetic field by means of a receiver coil, which detected magnetic field thereby generates a signal in the receiver coil,
  determining a first characteristic value of the signal in a first time range, the first time range starting at a time:
    at which it has been estimated that any disturbances due to control of the current to obtain the second magnitude have ceased, and
    a current induced in the metallic material due to control of the current to obtain the second magnitude has penetrated deeper in the metallic material than a depth corresponding to surface irregularities of the metallic material and crack depths not desired to be measured,
    the first time range ending when the current induced in the metallic material due to control of the current to obtain the second magnitude has penetrated to a depth in the metallic material corresponding to a deepest crack depth desired to be measured,
  determining a second characteristic value of the signal in a second time range after the first time range, and
  determining a possible presence of a crack and its crack depth based on the first characteristic value and the second characteristic value.

By determining the first characteristic value and the second characteristic value according to the above specified time ranges, a crack depth may be determined independently without having other process parameters affecting the determined crack depth value. Hence reliable crack depth measurements may be provided.

In one embodiment, in the step of feeding, the current is essentially constant.

In one embodiment the estimation of the magnetic field having penetrated deeper than a deepest crack depth desired to be measured in the metallic material is based on when the feeding the current to the transmitter coil starts, a deepest crack depth desired to be measured and the relative permeability and electrical resistivity of the metallic material.

In one embodiment the start of the first time range is estimated based on a time when control of the current to obtain its second magnitude starts and on a relation between the relative permeability and electrical resistivity of the metallic material.

In one embodiment the end of the first time range is estimated based on the time when the current obtains its second magnitude, the deepest crack depth desired to be measured and the relative permeability and electrical resistivity of the metallic material.

In one embodiment the step of determining the first characteristic value comprises integrating the signal during the first time range.

In one embodiment the step of determining the second characteristic value comprises integrating the signal during the second time range.

In one embodiment the step of determining a possible presence of a crack and its crack depth involves determining a relation between the first characteristic value and the second characteristic value.

One embodiment comprises determining a third characteristic value of the signal in a third time range, the third time range starting simultaneously with the first time range and ending at a time which is determined based on the start of the first time range and the end of the first time range, wherein the step of determining comprises determining a crack length of a possible crack based on the first characteristic value, the second characteristic value and the third characteristic value. By determining a third characteristic value as specified above, crack depth of a crack having a shorter extension than the extension of the receiver coil in a plane parallel with the surface of the metallic material to be inspected may be determined. Moreover, the third characteristic value also provides sufficient information together with the first characteristic value and the second characteristic value to be able to determine the crack length.

In one embodiment the step of determining the third characteristic value comprises integrating the signal during the third time range.

According to a second aspect of the present disclosure there is provided an arrangement for determining a crack depth of a crack in a metallic material, the arrangement comprising: a transmitter coil arranged to generate a magnetic field in the metallic material; a receiver coil arranged to detect the magnetic field; a signal generator arranged to feed a current having a first magnitude to the transmitter coil for generating the magnetic field in the metallic material; a control unit arranged to control the signal generator such that the current obtains a second magnitude when the magnetic field is estimated to have penetrated deeper than a deepest crack depth desired to be measured in the metallic material; and a computing arrangement arranged to receive a signal created by the magnetic field detected by the receiver coil, and to determine a first characteristic value of the signal in a first time range, the first time range starting at a time:

at which it has been estimated that any disturbances due to control of the current to obtain the second magnitude have ceased, and a current induced in the metallic material due to control of the current to obtain the second magnitude has penetrated deeper in the metallic material than a depth corresponding to surface irregularities of the metallic material and crack depths not desired to be measured, the first time range ending after the current induced in the metallic material due to control of the current to obtain the second magnitude has penetrated to a depth in the metallic material corresponding to a deepest crack depth desired to be measured, the computing arrangement being further arranged to determine a second characteristic value of the signal in a second time range after the first time range, and to determine a possible presence of a crack and its crack depth based on the first characteristic value and the second characteristic value.

In one embodiment the computing arrangement is arranged to determine a third characteristic value of the signal in a third time range, the third time range starting simultaneously with the first time range and ending at a time which is determined based on the start of the first time range and the end of the first time range, and to determine a crack length of a possible crack based on the first characteristic value, the second characteristic value and the third characteristic value.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

The inventive concept will now be described, by way of example, with reference to the accompanying drawings, in which.

DETAILED DESCRIPTION OF THE INVENTION

Figure 1:
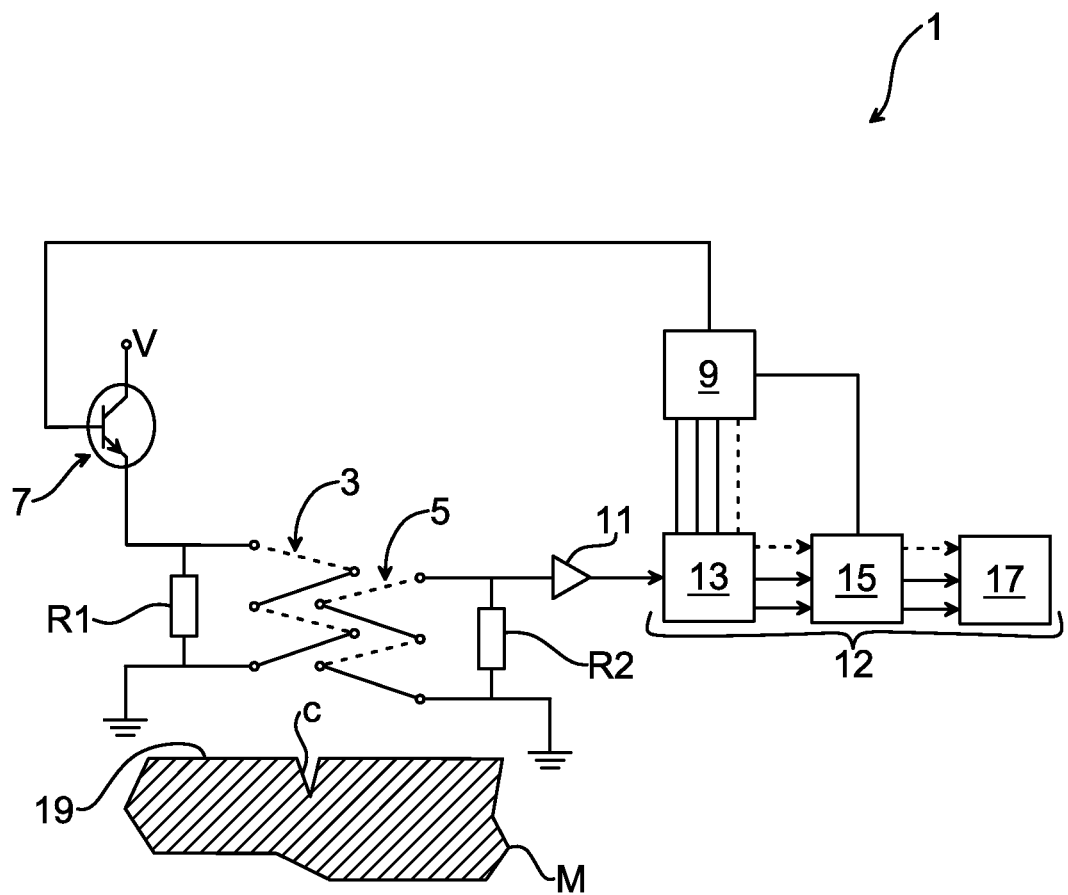
FIG. 1 is a schematic view of an example of an arrangement for crack detection in a metallic material.

The inventive concept will now be described more fully hereinafter with reference to the accompanying drawings, in which certain embodiments of the inventive concept are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art.

The arrangement presented herein is adapted to detect cracks in a metallic material by determining the crack depth of a crack. The arrangement may in some embodiments also be able to determine the crack length. Advantageously, the arrangement may be used under extreme conditions, for instance in a metal making process such as a casting process or a rolling process. The arrangement may in particular be used for accurate crack depth measurement of cracks on rough metallic surfaces.

Any metallic material which has a conductivity which is high enough to allow a current to be induced in the metallic material may be inspected by means of the methods and arrangements presented herein.

FIG. 1a shows a schematic view of an example of an arrangement for detecting cracks in a surface 19 of a metallic material M. Arrangement 1 comprises signal generator 7 arranged to generate an output signal, a control unit 9 arranged to control the output signal of the signal generator 7, a transmitter coil 3 arranged to receive the output signal from the signal generator 7 to thereby generate a magnetic field in a metallic material M which is to be inspected for cracks, a first resistor R1, a receiver coil 5 arranged to detect the magnetic field and to create a signal based on the detected magnetic field, a second resistor R2, an amplifier 11 arranged to amplify the signal from the receiver coil 5, and a computing arrangement 12 arranged to process the signal from the amplifier 11 in order to determine whether a crack is present in the metallic material by determining a possible crack depth. The computing arrangement 12 may comprise various subunits such as a first unit 13, a second unit 15, and a third unit 17.

In general, the present disclosure involves the generation of a magnetic field in the metallic material M, detecting the magnetic field, and determining characteristic values of a signal pertaining to the detected magnetic field in certain predetermined time ranges to thereby be able to determine a crack depth, and in some embodiments also a crack length, as will be detailed in the following.

Examples of the operation of the arrangement 1 will now be described in more detail with reference to FIGS. 1-3. The metallic material M, for instance a slab or a metal sheet, which is to be inspected for cracks C, is placed in the vicinity of the transmitter coil 3 and the receiver coil 5.

The metallic material M may in one embodiment move in relation to the transmitter coil 3 and receiver coil 5 during crack inspection to thereby enable inspection along the surface 19 of the metallic material M.

The control unit 9 is arranged to provide a control signal to the signal generator 7 to thereby control the output signal, e.g. a current, of the signal generator 7 provided to the transmitter coil 3. The signal generator 7 may for instance comprise a transistor which may be controlled by the control unit 9 to be in an open state and thereby provide a current to the transmitter coil 3 or a closed state in which it does not provide a current to the transmitter coil 3.

Figure 2A:
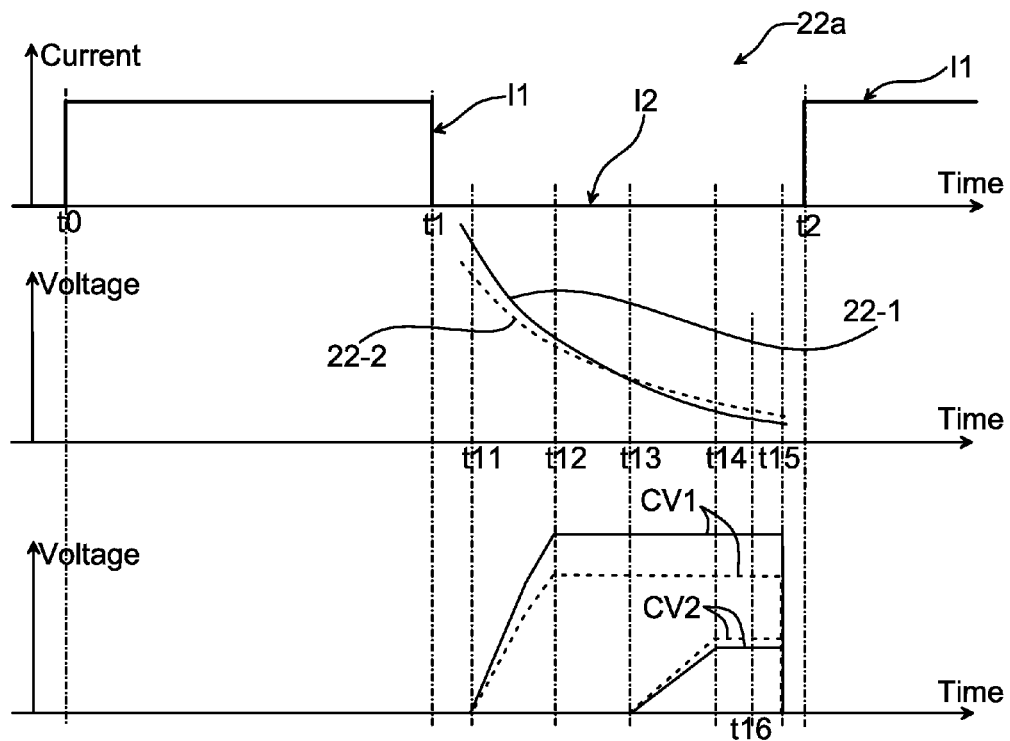
FIGS. 2a and 2b show diagrams of first, second, and third time ranges for determining characteristic values of a signal detected by the arrangement in FIG. 1.
Figure 3:
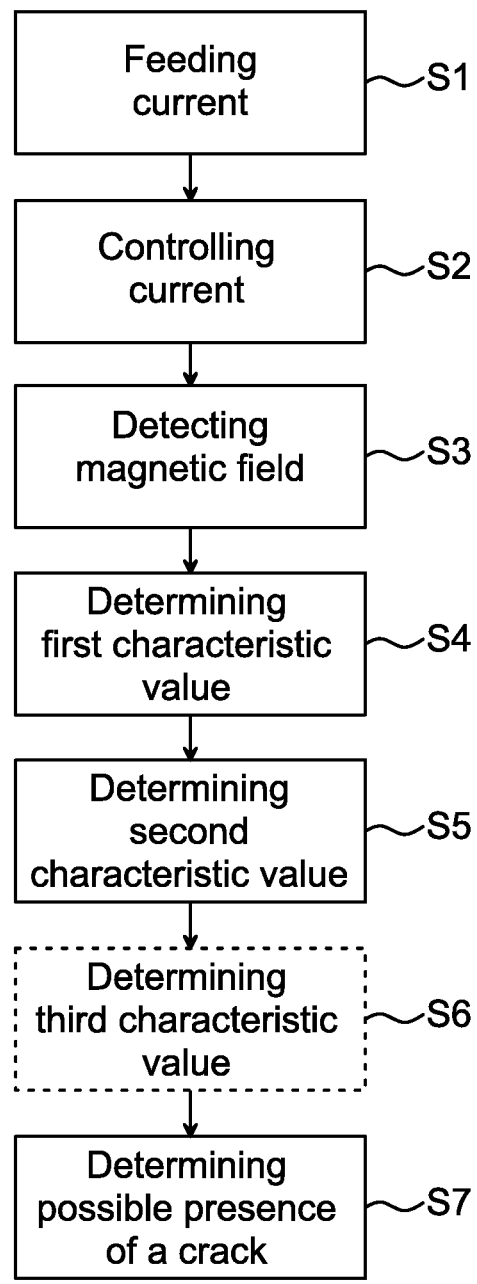
FIG. 3 is a flowchart of methods of determining a crack depth in a metallic material.

In one embodiment the control unit 9 is arranged to control the signal generator 7 such that the signal generator generates a current which is essentially constant having a first magnitude I1 in a first time span $t_1$-$t_0$, as shown in FIG. 2a.

In a first step S1 the current with the first magnitude I1 is fed to the transmitter coil 3. A magnetic field is thereby created in the metallic material M. During crack inspection, the surface 19 of the metallic material M is arranged sufficiently close to the transmitter coil 3 such that the magnetic field around the transmitter coil 3 is able to penetrate into the metallic material M thus causing the magnetic field in the metallic material M.

At a point in time $t_1$ when it is estimated that the magnetic field has penetrated deeper into the metallic material M than the deepest crack depth desired to be measured in the metallic material M, the current fed by the signal generator 7 is in a second step S2 controlled by the control unit 9 such that the essentially constant current obtains a second magnitude I2. The second magnitude I2 may for example be essentially zero or zero. The second step S2 may hence involve setting the transistor in its closed state. The change of current feed from the first amplitude I1 to the second amplitude I2 causes an induced current to be generated in the metallic material M.

The current which is fed by the signal generator 7 is preferably in the form of a pulse train 22a as shown in the uppermost diagram in FIG. 2a. Measurements of the magnetic field are typically taken between subsequent pulses, as will be elaborated in more detail in the following.

The estimation of when the magnetic field has penetrated deeper into the metallic material M than the deepest crack depth desired to be measured in the metallic material M may be based on theoretical estimation, with the estimated time being programmed in a software in the control unit 9 such that it can control the current output by the signal generator 7 accordingly.

Figure 2B:
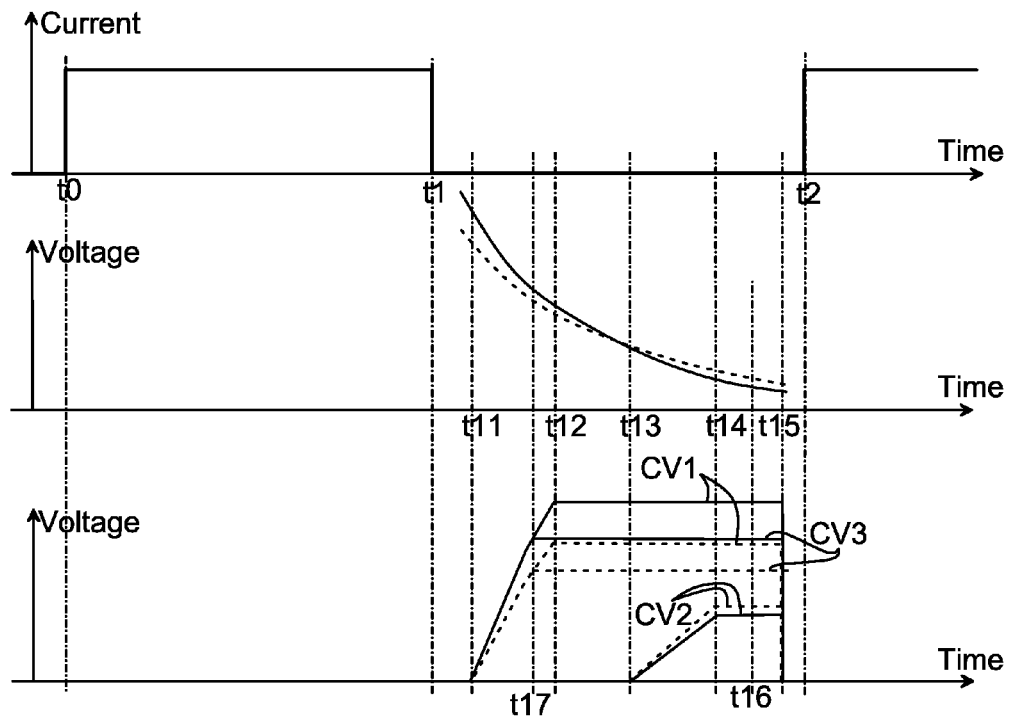

The estimation may be based on when the feeding of the current to the transmitter coil 3 starts, a deepest crack depth desired to be measured, the relative permeability μ and electrical resistivity ρ of the metallic material M. Such estimation may for instance be provided by the following relation:

$$t_1 - t_0 > 1.5 * \mu * (CD_{max})^2 / \rho,$$

where $t_1$ is the time in milliseconds when the current obtains its second magnitude I2, as shown in FIGS. 2a-b, $t_0$ is the time when the current obtains its first magnitude I1, $CD_{max}$ is the maximum crack depth desired to be measured in millimeter, μ is the relative permeability of the metallic material M, and ρ is the electrical resistivity of the metallic material M in nano Ohm meter, nΩm.

Following the second step S2, the energy in the transmitter coil 3 can quickly be discharged by means of the first resistor R1. The first resistor R1 is hence arranged to discharge the energy from the transmitter coil 3 when the current has attained its second magnitude I2. In one embodiment the first resistor R1 may be arranged in parallel connection with the transmitter coil 3.

In a third step S3, when the current has attained its second magnitude I2, the magnetic field created by the induced current is detected by the receiver coil 5. The magnetic field detected by the receiver coil 5 induces a signal, e.g. a voltage, in the receiver coil which may be amplified by means of the amplifier 11.

The amplifier 11 provides the amplified signal to the computing arrangement 12. The computing arrangement 12 is in one embodiment arranged to, in a fourth step S4 and in a fifth steps S5, determine a first characteristic value CV1 and a second characteristic value CV2, respectively, of the signal. In one embodiment the control unit 9 is arranged to provide control signals to the first unit 13 for the first unit 13 to be able to determine the first characteristic value CV1 in a first time range $t_{12}$-$t_{11}$, and the second characteristic value CV2 in a second time range $t_{14}$-$t_{13}$ as shown in FIGS. 2a-b.

Prior to, or concurrently with the detection of the magnetic field by the receiver coil 5 in the third step S3, the energy created in the receiver coil 5 by the magnetic field is discharged by means of the second resistor R2. The second resistor R2 is hence arranged to discharge the energy from the receiver coil 5 when the current has attained its second magnitude I2. In one embodiment the second resistor R2 may be arranged in parallel connection with the receiver coil 5.

By means of proper selection of resistance of the first resistor R1 and the second resistor R2 and a fast switching between the first magnitude I1 and the second magnitude I2 of the current, a fast discharge of the energy in the transmitter coil 3 and the receiver coil 5 may be achieved, thus allowing for a short time span $t_{11}$-$t_1$ before commencement of magnetic field measurements by means of the receiver coil 5.

The start $t_{11}$ of the first time range $t_{12}$-$t_{11}$ is in one embodiment at a time at which it has been estimated that any disturbances due to control of the current to obtain the second magnitude I2 have ceased, and the induced current in the metallic material M due to control of the current to obtain the second magnitude I2 has penetrated deeper in the metallic material M than a depth corresponding to surface irregularities of the metallic material M and shallow crack depths not desired to be measured.

Each start point and end point of the time ranges described herein are typically programmed in the software of the control unit 9, which can provide control signals to the computing arrangement 12, e.g. the first unit 13 to determine the first characteristic value CV1, the second characteristic value CV2, and in embodiments where a third characteristic value CV3 is determined, also to determine the third characteristic value CV3.

Estimation of the time when the current has penetrated to a depth deeper than surface irregularities of the metallic material M and shallow crack depths not desired to be measured may be provided by the following relation in case crack depths and surface irregularities having a depth of less than or equal to 1 mm are not desired to be measured:

$$t_{11} - t_1 \approx 0.2 * \mu / \rho,$$

where $t_1$ is the time in milliseconds when the current is controlled to have a second magnitude I2, μ is the relative permeability of the metallic material M, and ρ is the electrical resistivity in nΩm. Similar equations can be derived depending on the minimum crack depth desired to be measured.

The first time range $t_{12}$-$t_{11}$ ends when the current induced in the metallic material due to control of the current to obtain the second magnitude has penetrated to a depth in the metallic material corresponding to a deepest crack depth desired to be measured. Estimation of the end $t_{12}$ of the first time range $t_{12}$-$t_{11}$ can for instance be made by the following relation:

$$t_{12}-t_1 \approx 0.2*\mu*(CD_{max})^2/\rho.$$

It is to be understood that with the terms estimation is generally meant a theoretical estimation of time ranges and pulse duration.

During the first time range $t_{12}$-$t_{11}$ the first characteristic value CV1 is determined by means of the computing arrangement 12, for instance by the first unit 13. The first characteristic value CV1 may be any of a single value of the signal taken in the first time range $t_{12}$-$t_{11}$, a mean value of the signal in the first time range $t_{12}$-$t_{11}$, or an integration of the signal in the first time range $t_{12}$-$t_{11}$.

In the middle diagram in FIG. 2a a continuous line 22-1 shows an example of a signal detected by the receiver coil 5 when a crack is present in the metallic material M, and a dashed line 22-2 shows an example of a signal detected by the receiver coil 5 when a crack C is not present in the metallic material M. The lowermost diagram in FIG. 2a shows an example where the signals of lines 22-1 and 22-2 are integrated during the first time range $t_{12}$-$t_{11}$ to thereby determine the first characteristic value CV1. It can be seen that the signal values differ when a crack is present compared to when no crack is present.

The commencement of the second time range $t_{14}$-$t_{13}$ is after the first time range $t_{12}$-$t_{11}$. In one embodiment there is an intermediate time range $t_{13}$-$t_{12}$, between the first time range $t_{12}$-$t_{11}$ and the second time range $t_{14}$-$t_{13}$ having a duration of the same magnitude as the duration of the first time range $t_{12}$-$t_{11}$, during which no samples of the signal are taken. Other durations of the intermediate time range may also be possible.

In the fifth step S5, the second characteristic value CV2 is determined in the second time range $t_{14}$-$t_{13}$, which is after the first time range $t_{12}$-$t_{11}$ and starts at a time $t_{13}$. The duration of the second time range is in one embodiment of the same magnitude as the first time range $t_{12}$-$t_{11}$. The second time range $t_{14}$-$t_{13}$ ends at a time $t_{14}$.

During the second time range $t_{14}$-$t_{13}$ the second characteristic value CV2 is determined by means of the computing arrangement 12, for instance by the first unit 13 and the second unit 15. The second characteristic value CV2 may be any of a single value of the signal taken in the second time range $t_{14}$-$t_{13}$, a mean value of the signal in the second time range $t_{14}$-$t_{13}$, or an integration of the signal in the second time range $t_{14}$-$t_{13}$.

The lowermost diagram in FIG. 2a shows an example where the signal with no cracks present and the signal where a crack is present are integrated during the second time range $t_{14}$-$t_{13}$ to thereby determine the second characteristic value CV2. It can be seen that the signal values differ when a crack is present compared to when no crack is present.

The first characteristic value CV1 and the second characteristic value CV2 are provided to the second unit 15. The first characteristic value CV1 and the second characteristic value CV2 may be provided in the form of an analog signal as a voltage by means of a sample-and-hold circuit arranged in the second unit 15, or alternatively as a digital signal by means of an A/D-converter arranged in the second unit 15.

The first characteristic value CV1 and the second characteristic value CV2 may be provided by the second unit 15 to the third unit 17 at a time $t_{16}$, wherein the first unit 13 can be reset at a time $t_{15}$ for a subsequent measurement, i.e. a determination of characteristic values of a subsequent current pulse. This is shown in the lowermost diagram in FIG. 2a.

In a step S7 it is determined whether a crack is present by determining the crack depth based on the first characteristic value CV1 and the second characteristic value CV2. The determination of the crack depth can be performed in the third unit 17 by means of determining a relation between the first characteristic value CV1 and the second characteristic value CV2.

The inventor has realised that the relation CV1/CV2 between the first characteristic value CV1 and the second characteristic value CV2 is independent of the distance of the transmitter coil 3 and receiver coil 5 from the surface 19 of the metallic material M, the resistivity p of the metallic material M, and possible irregularities on the surface 19 of the metallic material M. A relation between the first characteristic value CV1 and the second characteristic value CV2 may therefore beneficially be used for determining the crack depth in cases where the crack length is relatively large in relation to the extension of the receiver coil 3 in a plane parallel with the surface 19 of the metallic material M when inspecting the metallic material M for cracks. The crack depth CD may in particular be determined by means of for example the following expression:

$$CD \approx C1*(CV1/CV2-C2),$$

where C1 and C2 are two constants. C2 is determined in such a way that the crack depth CD becomes zero when no crack is present in a measurement of the metallic material M. C1 may be determined by measuring a crack depth with a known depth or by theoretical calculations. The constants C1 and C2 may for instance be stored in a memory of the third unit 17 to thereby be used in computation of the crack depth.

In one embodiment, especially suitable for determining crack depths of cracks having a length extension which is smaller than the a dimension of the receiver coil 3 in a plane parallel with a the surface 19 of the metallic material M when inspecting the metallic material M for cracks, a third characteristic value CV3 may be determined by means of the computing arrangement 12 in a step S6 prior to the step S7 of determining the crack depth. The third characteristic value CV3 is determined in a third time range $t_{17}$-$t_{11}$ which starts at time $t_{11}$ when the first time range $t_{12}$-$t_{11}$ starts and ends at a time $t_{17}$ before the ending $t_{12}$ of the first time range $t_{12}$-$t_{11}$, as shown in the lowermost diagram in FIG. 2b.

During the third time range $t_{11}$-$t_{17}$ the third characteristic value CV3 is determined by means of the computing arrangement 12, for instance by the first unit 13, via initiation by control signals from the control unit 9. The third characteristic value CV3 may be any of a single value of the signal taken in the third time range $t_{17}$-$t_{11}$, a mean value of the signal in the third time range $t_{17}$-$t_{11}$, or an integration of the signal in the third time range $t_{17}$-$t_{11}$. The end $t_{17}$ of the third time range $t_{17}$-$t_{11}$ may be determined based on the time $t_{11}$ of the start of the first time range $t_{12}$-$t_{11}$, and the time of ending $t_{12}$ of the first time range $t_{12}$-$t_{11}$. An example of a relation for determining the end $t_{17}$ of the third time range is:

$$t_{17} = \left(\frac{\sqrt{t_{12}} + \sqrt{t_{11}}}{2}\right)^2.$$

In an embodiment where the third characteristic value CV3 has been determined in step S6, also the crack length may be determined in step S7. The step S7 of determining the crack length of a possible crack may be based on the first characteristic value CV1, the second characteristic value CV2 and the third characteristic value CV3. The crack length CL may for instance be determined by the following relation:

$$CL = C3 \cdot \frac{2*CV3 - CV1}{CV2},$$

and the crack depth CD may be determined by:

$$CD = C4 \cdot \frac{CV1}{2*CV3 - CV2},$$

where C3 and C4 are constants. The constants C3 and C4 may be determined by means of empirical studies, e.g. by measurements of known crack depths and crack lengths of cracks in a metallic material. The constants C3 and C4 may be stored in a memory of the computing arrangement 12, e.g. in a memory of the third unit 17.

In order to be able to obtain a crack depth or crack length measure, relations between the first characteristic value CV1 and the second characteristic value CV2 in the form of a relation CV1/CV2 and a relation CV1/CV3 between the first characteristic value CV1 and the third characteristic value CV3 for known crack depths and crack lengths may be provided in a data structure e.g. a table, wherein interpolation of crack depths and crack lengths may be performed based on the values in the data structure.

A current pulse is at a time $t_2$ fed by the signal generator 7 to the transmitter coil 3, wherein the above steps S1-S5 and S7 are repeated. In embodiment where the crack length is shorter than the extension of the receiver coil 3 also step S6 is repeated.

The inventive concept has mainly been described above with reference to a few embodiments. However, as is readily appreciated by a person skilled in the art, other embodiments than the ones disclosed above are equally possible within the scope of the invention, as defined by the appended claims.

What is claimed is:

1. A method of determining a crack depth of a crack in a metallic material, the method comprising:
   feeding a current with a first magnitude to a transmitter coil for generating a magnetic field in the metallic material,
   controlling the current such that it obtains a second magnitude when the magnetic field is estimated to have penetrated deeper than a deepest crack depth desired to be measured in the metallic material,
   detecting the magnetic field by means of a receiver coil, which detected magnetic field thereby generates a signal in the receiver coil,
   determining a first characteristic value of the signal in a first time range, the first time range starting at a time:
      at which it has been estimated that any disturbances due to control of the current to obtain the second magnitude have ceased, and
      a current induced in the metallic material due to control of the current to obtain the second magnitude has penetrated deeper in the metallic material than a depth corresponding to surface irregularities of the metallic material and crack depths not desired to be measured,
   the first time range ending when the current induced in the metallic material due to control of the current to obtain the second magnitude has penetrated to a depth in the metallic material corresponding to a deepest crack depth desired to be measured,
   determining a second characteristic value of the signal in a second time range after the first time range, and
   determining a possible presence of a crack and its crack depth based on the first characteristic value and the second characteristic value.

2. The method as claimed in claim 1, wherein in the step of feeding, the current is essentially constant.

3. The method as claimed in claim 1, wherein the estimation of the magnetic field having penetrated deeper than a deepest crack depth desired to be measured in the metallic material is based on when the feeding the current to the transmitter coil starts, a deepest crack depth desired to be measured and the relative permeability and electrical resistivity of the metallic material.

4. The method as claimed in claim 1, wherein the start of the first time range is estimated based on a time when control of the current to obtain its second magnitude starts and on a relation between the relative permeability and electrical resistivity of the metallic material.

5. The method as claimed in claim 1, wherein the end of the first time range is estimated based on the time when the current obtains its second magnitude, the deepest crack depth desired to be measured and the relative permeability and electrical resistivity of the metallic material.

6. The method as claimed in claim 1, wherein the step of determining the first characteristic value comprises integrating the signal during the first time range.

7. The method as claimed in claim 1, wherein the step of determining the second characteristic value comprises integrating the signal during the second time range.

8. The method as claimed in claim 1, wherein the step of determining a possible presence of a crack and its crack depth involves determining a relation between the first characteristic value and the second characteristic value.

9. The method as claimed in claim 1, comprising:
   determining a third characteristic value of the signal in a third time range, the third time range starting simultaneously with the first time range and ending at a time which is determined based on the start of the first time range and the end of the first time range, wherein the step of determining comprises determining a crack length of a possible crack based on the first characteristic value, the second characteristic value and the third characteristic value.

10. The method as claimed in claim 9, wherein the step of determining the third characteristic value comprises integrating the signal during the third time range.

11. An arrangement for determining a crack depth of a crack in a metallic material, the arrangement comprising:
   a transmitter coil arranged to generate a magnetic field in the metallic material,
   a receiver coil arranged to detect the magnetic field,
   a signal generator arranged to feed a current having a first magnitude to the transmitter coil for generating the magnetic field in the metallic material,
   a control unit arranged to control the signal generator such that the current obtains a second magnitude when the magnetic field is estimated to have penetrated deeper than a deepest crack depth desired to be measured in the metallic material, and
   a computing arrangement arranged to receive a signal created by the magnetic field detected by the receiver coil, and to determine a first characteristic value of the signal in a first time range, the first time range starting at a time:
      at which it has been estimated that any disturbances due to control of the current to obtain the second magnitude have ceased, and a current induced in the metallic material due to control of the current to obtain the second magnitude has penetrated deeper in the metallic material than a depth corresponding to surface irregularities of the metallic material and crack depths not desired to be measured, the first time range ending after the current induced in the metallic material due to control of the current to obtain the second magnitude has penetrated to a depth in the metallic material corresponding to a deepest crack depth desired to be measured, the computing arrangement being further arranged to determine a second characteristic value of the signal in a second time range after the first time range, and to determine a possible presence of a crack and its crack depth based on the first characteristic value and the second characteristic value.

12. The arrangement as claimed in claim 11, wherein the computing arrangement is arranged to determine a third characteristic value of the signal in a third time range, the third time range starting simultaneously with the first time range and ending at a time which is determined based on the start of the first time range and the end of the first time range, and to determine a crack length of a possible crack based on the first characteristic value, the second characteristic value and the third characteristic value.

* * * * *